(12) United States Patent
Han

(10) Patent No.: US 9,020,784 B2
(45) Date of Patent: Apr. 28, 2015

(54) METHODS FOR PROVIDING A BONDED-PARTICLE MODEL IN COMPUTER AIDED ENGINEERING SYSTEM

(71) Applicant: Zhidong Han, Livermore, CA (US)

(72) Inventor: Zhidong Han, Livermore, CA (US)

(73) Assignee: Livermore Software Technology Corp., Livermore, CA (US)

( * ) Notice: Subject to any disclaimer, the term of this patent is extended or adjusted under 35 U.S.C. 154(b) by 382 days.

(21) Appl. No.: 13/626,570

(22) Filed: Sep. 25, 2012

(65) Prior Publication Data

US 2013/0289957 A1 Oct. 31, 2013

Related U.S. Application Data

(60) Provisional application No. 61/639,777, filed on Apr. 27, 2012.

(51) Int. Cl.
*G06F 17/50* (2006.01)
*G06F 19/00* (2011.01)

(52) U.S. Cl.
CPC .......... *G06F 17/5009* (2013.01); *G06F 19/701* (2013.01); *G06F 2217/16* (2013.01)

(58) Field of Classification Search
CPC ............ G06F 17/5018; G06F 2217/16; G06F 17/5009; G06F 19/701
USPC ........................................................... 703/2
See application file for complete search history.

(56) References Cited

U.S. PATENT DOCUMENTS

| 7,516,053 B1 * | 4/2009 | Lu ..................................... 703/6 |
| 2011/0077918 A1 * | 3/2011 | Mutlu et al. ...................... 703/2 |

OTHER PUBLICATIONS

Cundall, P. A. "A discontinuous future for numerical modelling in geomechanics?." Proceedings of the ICE-Geotechnical Engineering 149.1 (2001): 41-47.*
Potyondy, D. O., and P. A. Cundall. "A bonded-particle model for rock." International journal of rock mechanics and mining sciences 41.8 (2004): 1329-1364.*

* cited by examiner

*Primary Examiner* — Aniss Chad
(74) *Attorney, Agent, or Firm* — Roger H. Chu

(57) ABSTRACT

Systems and methods of providing bonded-particle model amongst a plurality of discrete particles representing a physical domain made of brittle material in a time-marching simulation to obtain numerically simulated continuum physical phenomena are disclosed. A physical domain is represented by a plurality of discrete particles. A domain of influence is assigned to each discrete particle and a bonded-particle model is created for the discrete particles. Respective bonds are established to connect each discrete particle to all other discrete particles within its domain of influence. The bonded-particle model further defines a rule for breakage of a bond. Continuum physical phenomena of the physical domain are numerically represented through a set of formula such that a time-marching simulation of the physical domain can be conducted. Physical properties include material properties and fracture energy release rate. Finally, the bonded-particle model allows size and orientation changes of each discrete particle.

20 Claims, 7 Drawing Sheets

METHODS FOR PROVIDING A BONDED-PARTICLE MODEL IN COMPUTER AIDED ENGINEERING SYSTEM

FIELD OF THE INVENTION

The present invention generally relates to computer-aided engineering analysis, more particularly to systems and methods of providing a bonded-particle model amongst a plurality of discrete particles that represents a physical domain made of brittle material in a time-marching simulation to obtain numerically simulated physical phenomena.

BACKGROUND OF THE INVENTION

Many modern engineering analyses are performed with the aid of a computer system. One of such computer aided engineering (CAE) analyses is referred to as discrete element method (DEM) or distinct element method, which is generally used for numerically simulating the motion of a large number of discrete particles. With advances in computing power and numerical algorithms for nearest neighbor sorting, it has become possible to numerically simulate millions of discrete particles. Today DEM is becoming widely accepted as an effective method of addressing engineering problems in granular and discontinuous materials, especially in crack propagation, granular flows, powder mechanics, and rock mechanics.

The classic mechanics are based on solving Partial Differential Equations (PDEs) over the domain with the assumption of continuous distribution of mass, including finite element methods, boundary integral methods, meshless methods, and so on. In other disciplines, molecular dynamics (MD) have been used for determining the forces and energy atoms and molecules for simulations spanning nano-level to micro-level, which are not suitable for macro-level simulations.

In contrast, DEM offers a different approach that does not require formulation of a PDEs for continuum mechanics. However, there are drawbacks or shortcomings in prior art approaches. In particular, there is no integrated technique to bridge the continuum mechanics and fractured particles after the continuum has been damaged. Many ad hoc methods have been proposed, but none of these prior art approaches is satisfactory. For example, one of the prior art approaches assumes the forces acting on particles are axial only, hence not being able to simulate a domain having any relative shear deformation or lateral deformation correctly.

It would, therefore, be desirable to have systems and methods of providing an improved model amongst a plurality of discrete particles that represents a physical domain made of brittle material in a time-marching simulation to obtain numerically simulated continuum physical phenomena.

BRIEF SUMMARY OF THE INVENTION

This section is for the purpose of summarizing some aspects of the present invention and to briefly introduce some preferred embodiments. Simplifications or omissions in this section as well as in the abstract and the title herein may be made to avoid obscuring the purpose of the section. Such simplifications or omissions are not intended to limit the scope of the present invention.

The present invention discloses systems and methods of providing a bonded-particle model amongst a plurality of discrete particles representing a physical domain made of brittle material in a time-marching simulation to obtain numerically simulated continuum physical phenomena.

According to one aspect of the present invention, a physical domain is represented by a plurality of discrete particles. A domain of influence is assigned to each discrete particle and a bonded-particle model is created for the discrete particles. Respective bonds are established to connect each discrete particle to all other discrete particles within its domain of influence. The bonded-particle model further defines a rule for breakage of a bond.

Continuum physical phenomena (e.g., mechanical behaviors) of the physical domain are numerically represented through a set of formula (i.e., governing the discrete particles with the bonded-particle model) such that a time-marching simulation of the physical domain can be conducted. Physical properties include material properties and fracture energy release rate. The set of formula is used for calculating forces between each pair of discrete particles, and potential energy of the physical domain. Conservation of moment and energy balances of the physical domain are preserved. Finally, the bonded-particle model allows size and orientation changes of each discrete particle.

The bonded-particle model in accordance with one embodiment of the present invention is based on the physical properties of a material represented by the plurality of discrete particles with the following features:

1) Properties of the bond between each pair of discrete particles are determined by the material constants, including bulk modulus, shear modulus, and density. The strength of the bond is based on the material's fracture toughness in form of fracture energy release rate;
2) All discrete particles are free to move individually in the physical domain;
3) There are no differential operations in the bonded-particle model (i.e., no PDEs); and
4) There are no integral operations in the bonded-particle model for computational efficiency.

Objects, features, and advantages of the present invention will become apparent upon examining the following detailed description of an embodiment thereof, taken in conjunction with the attached drawings.

BRIEF DESCRIPTION OF THE DRAWINGS

These and other features, aspects, and advantages of the present invention will be better understood with regard to the following description, appended claims, and accompanying drawings as follows:

DETAILED DESCRIPTION

In the following description, numerous specific details are set forth in order to provide a thorough understanding of the present invention. However, it will become obvious to those skilled in the art that the present invention may be practiced without these specific details. The descriptions and representations herein are the common means used by those experienced or skilled in the art to most effectively convey the substance of their work to others skilled in the art. In other instances, well-known methods, procedures, components, and circuitry have not been described in detail to avoid unnecessarily obscuring aspects of the present invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments mutually exclusive of other embodiments. Further, the order of blocks in process flowcharts or diagrams representing one or more embodiments of the invention do not inherently indicate any particular order nor imply any limitations in the invention.

Embodiments of the present invention are discussed herein with reference to FIGS. 1-9. However, those skilled in the art will readily appreciate that the detailed description given herein with respect to these figures is for explanatory purposes as the invention extends beyond these limited embodiments.

Figure 1:
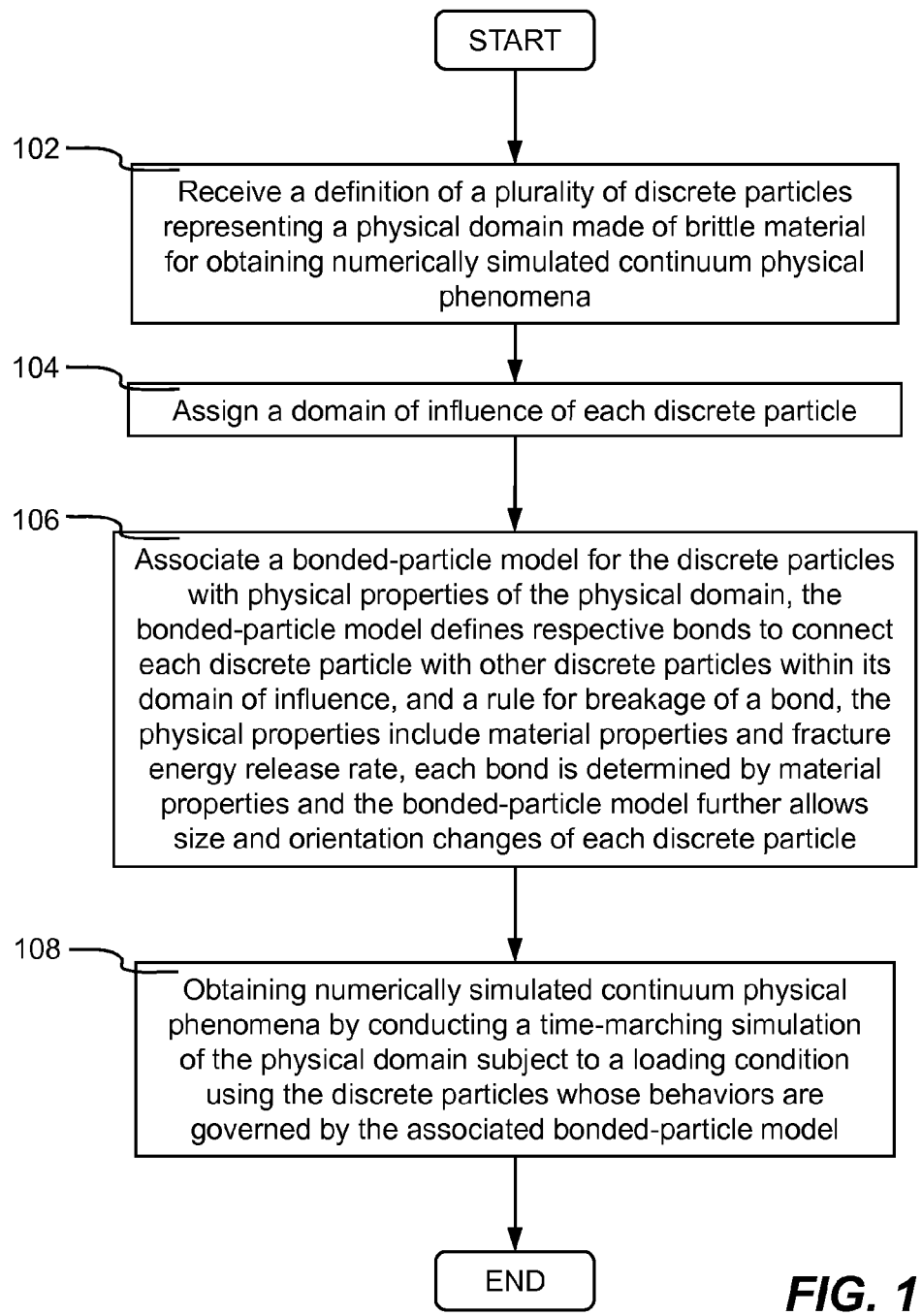
FIG. 1 is a flowchart illustrating an exemplary process of providing a bonded-particle model amongst a plurality of discrete particles used for numerically simulating continuum physical phenomena in accordance with one embodiment of the present invention.

Referring first to FIG. 1, it is shown a flowchart illustrating an exemplary process 100 of providing a bonded-particle model amongst a plurality of discrete particles representing a physical domain made of brittle material in a time-marching simulation to obtain numerically simulated continuum physical phenomena, according to an embodiment of the present invention. Process 100 is implemented in software and preferably understood with other figures.

Figure 8:
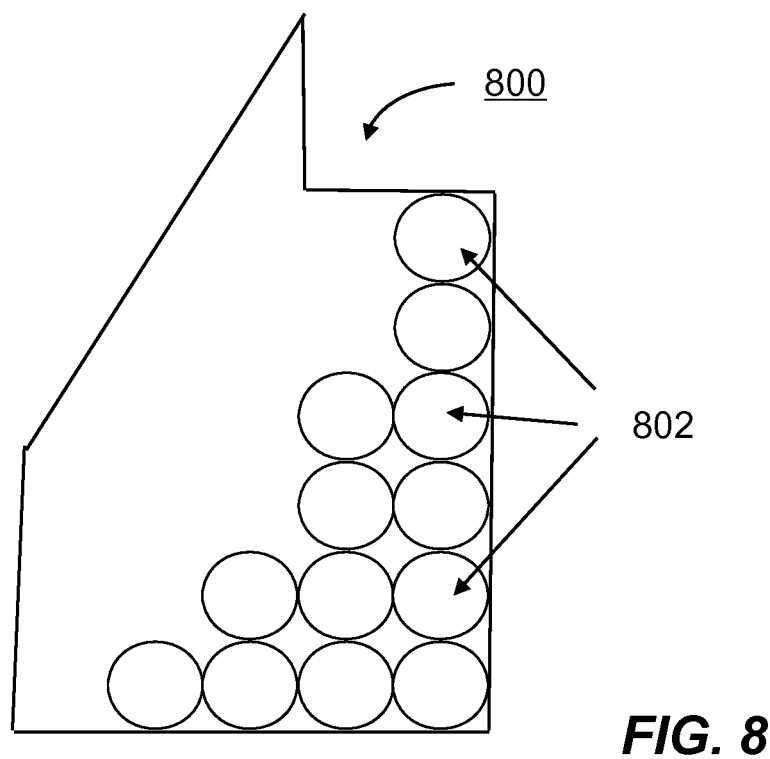
FIG. 8 is a two-dimensional diagram showing a plurality of discrete particles representing an exemplary physical domain in accordance with one embodiment of the present invention.

Process 100 starts by receiving a definition of a plurality of discrete particles that represents a physical domain made of brittle material at step 102. Physical domain can have any size or shape. FIG. 8 shows a plurality of discrete particles 802 (circles or discs) representing a physical domain 800 (an irregular geometric shape). For illustration simplicity, all examples used herein are in two-dimension and particles are circular or spherical. However, the present invention can apply to physical domain in two- or three-dimensions. And discrete particle can have a different geometric shape other than circular or spherical (e.g., rectangle, brick, etc.). Whereas the discrete particles 802 of FIG. 8 are arranged in uniformity, there is no such requirement in the present invention. Any other placement of discrete particles can achieve the same to represent a physical domain. The definition of the discrete particles includes each discrete particle's initial location, orientation and size.

Figure 2:
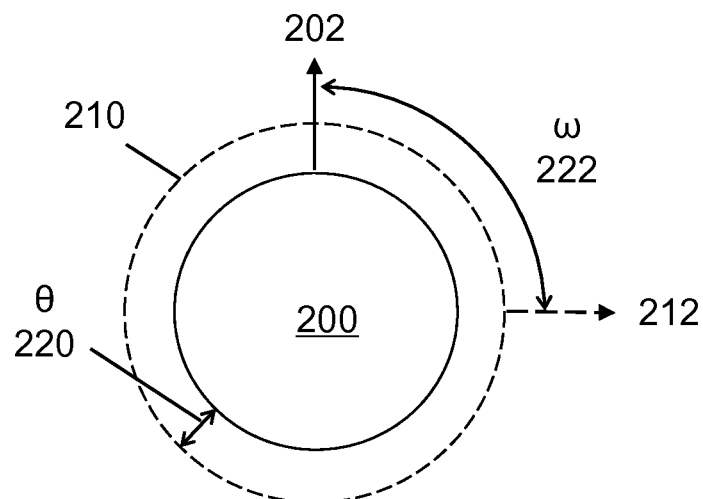
FIG. 2 is a two-dimensional diagram showing size and orientation changes of an exemplary discrete particle in a time-marching simulation, according to an embodiment of the present invention.

FIG. 2 shows an exemplary discrete particle (i.e., solid circle 200) having a first orientation 202 (indicated with a solid line arrow) and a second orientation 212 (indicated with a dotted line arrow). First and second orientations represent two different orientations of the discrete particle in a time-marching simulation, which starts initially at time zero and ends at a future time. For example, the first orientation can be the initial orientation at time zero "$t_0$", while the second is the orientation at another time "t". Or they can be two different orientations at two different times "$t_1$" and "$t_2$". The relative rotation ω 222 is between the first and the second orientations.

Also shown in FIG. 2 is first and second sizes of the exemplary discrete particle. First size is shown as solid circle 200 while the second size is shown in dotted line circle 210. In this example, the second size 210 is larger than the first size 200 (i.e., expansion). The second size can be smaller than the first size (i.e., shrinking) (not shown). The expansion/shrinkage θ 220 indicates the difference between the first size to the second size.

Figure 3:
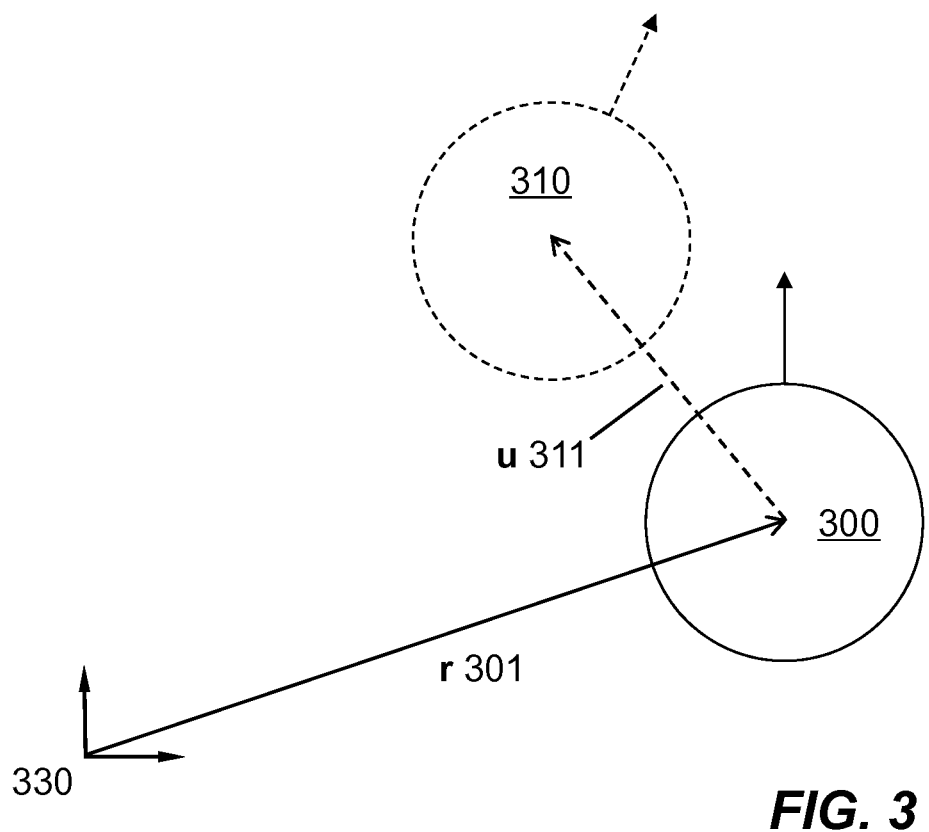
FIG. 3 is a two-dimensional diagram showing two exemplary locations of an exemplary discrete particle in a time-marching simulation, according to an embodiment of the present invention.

Shown in FIG. 3, it is a diagram illustrating first location 300 and second location 310 of an exemplary discrete particle in a global coordinate system 330. Well known schemes can be used for representing the locations. For example, vector r 301 is the first location 300 measured in a Cartesian coordinate system 330, while movement vector u 311 represents the second location 310 relative to the first location 300.

Referring back to FIG. 1, at step 104, a domain of influence is assigned to each discrete particle. This can be done by assigning a characteristic dimension to each discrete particle. For a circular or spherical domain, a characteristic dimension can be the radius.

Figure 4:
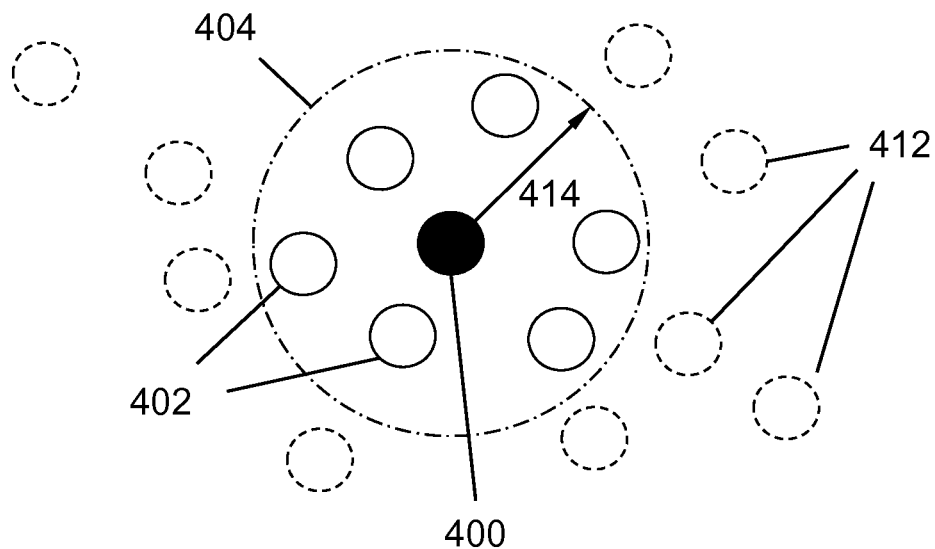
FIG. 4 is a two-dimensional diagram showing an exemplary domain of influence of an first exemplary discrete particle in accordance to one embodiment of the present invention.
Figure 7:
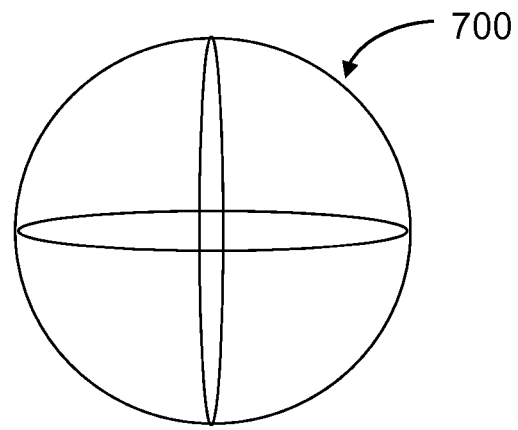
FIG. 7 is a diagram showing an exemplary three-dimensional discrete particle (i.e., a sphere) in accordance with one embodiment of the present invention.

FIG. 4 shows a first exemplary discrete particle 400 (solid black circle) is assigned a domain of influence (dotted line circular area 404). Discrete particles located within the domain of influence 404 are solid line circles 402, while discrete particles located outside the domain of influence 404 are dotted line circles 412. In this example, characteristic dimension is the radius 414 of the domain of influence 404. It is noted that the domain of influence is a volume instead of an area in three-dimension. The domain of influence 404 is used in a bonded-particle model to limit the number of neighboring discrete particles of any given discrete particle. Characteristic dimension can be constant for all discrete particles or different for each individual discrete particle. An exemplary three-dimensional discrete particle (i.e., sphere 700) is shown in FIG. 7.

Figure 5:
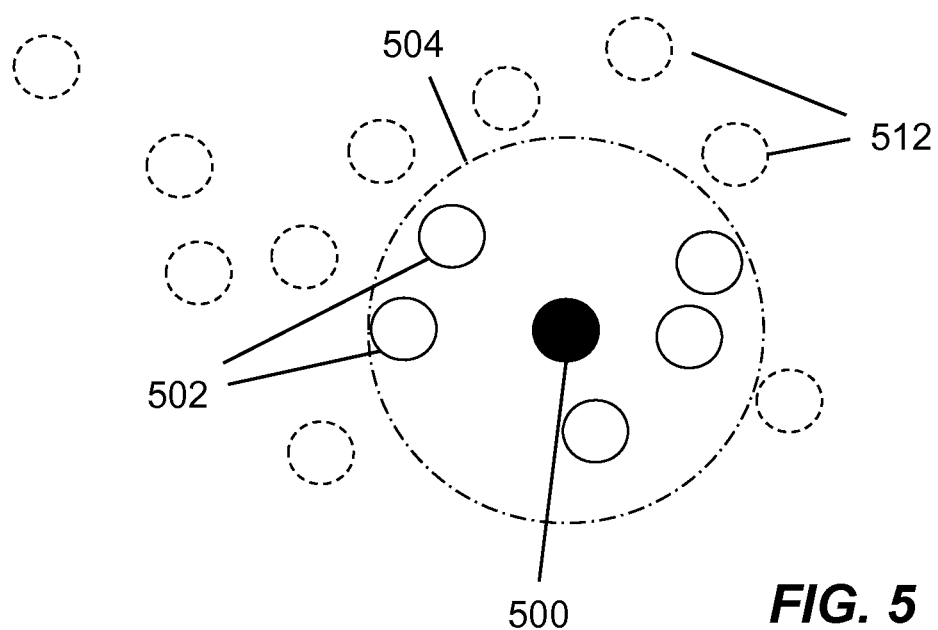
FIG. 5 is a two-dimensional diagram showing another exemplary domain of influence of a second exemplary discrete particle in accordance to one embodiment of the present invention.

A second exemplary discrete particle 500 is assigned a domain of influence 504 in FIG. 5. Similarly, discrete particles located outside the domain 504 are dotted line circles 512, while discrete particles located inside the domain 504 are solid line circles 502. It is noted that the set of discrete particles in FIG. 4 and in FIG. 5 are exactly the same. Each discrete particle of interest (e.g., particle 400 and particle 500) has its own domain of influence.

After the domain of influence has been assigned, a bonded-particle model for the discrete particles is associated with physical properties of the physical domain at step 106. The bonded-particle model establishes respective bonds to connect each discrete particle with all other discrete particles within its domain of influence. The bond is determined by the material properties, for example, bulk modulus, shear modulus, material density and fracture toughness. Further, the bonded-particle model defines a rule for breakage of a bond. The physical properties of a physical domain include material properties and fracture energy release rate of the physical domain's material.

Figure 6A:
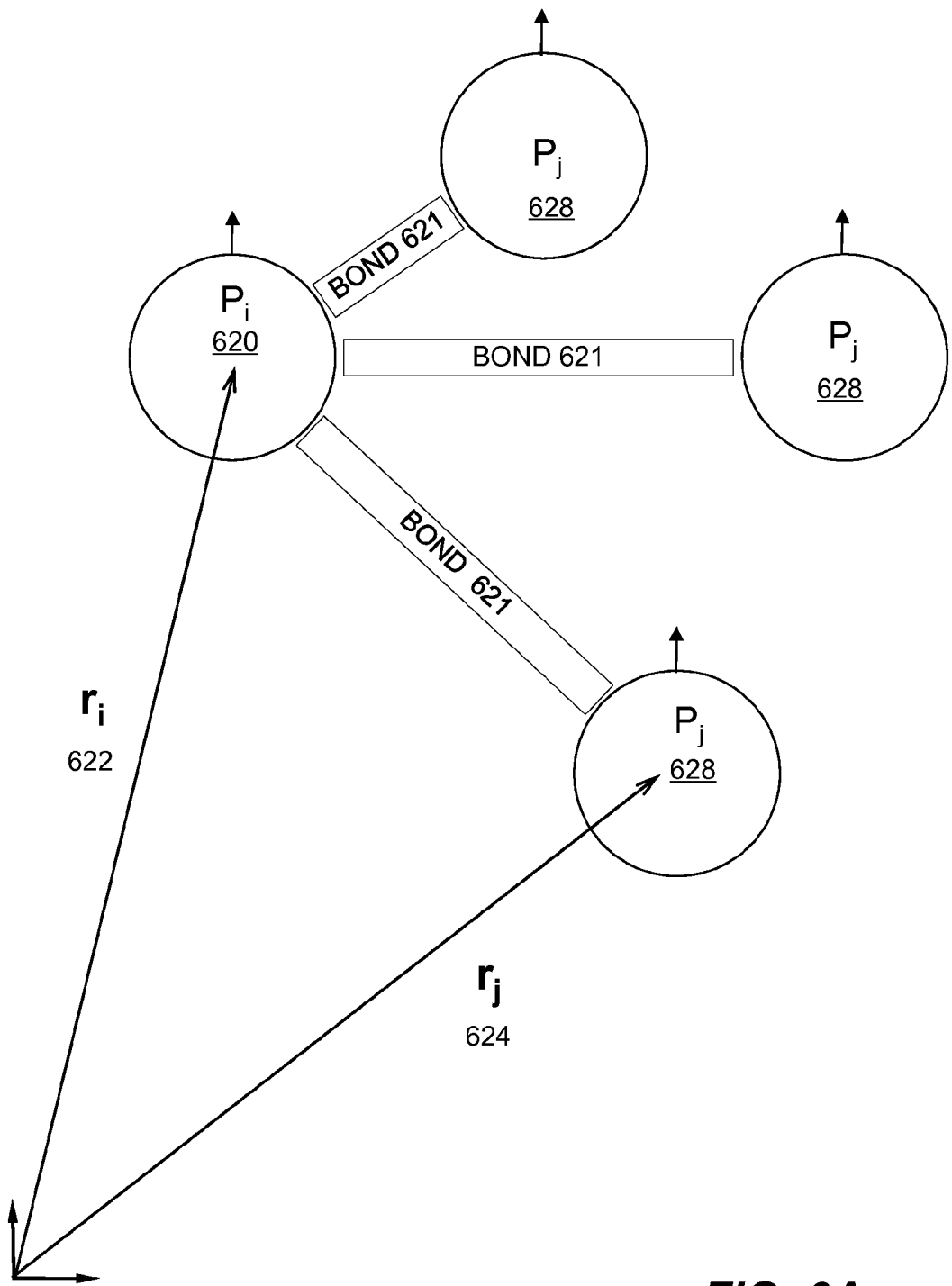
FIG. 6A is a two-dimensional diagram showing a first exemplary configuration of a discrete particle of interest based on a bonded-particle model, according to an embodiment of the present invention.

FIG. 6A shows a first exemplary configuration of a discrete particle of interest "Pi" 620 based on a bonded-particle model in accordance with one embodiment of the present invention. For illustration simplicity and clarity, the first exemplary configuration depicts three other discrete particles "Pj" 628 connected to the discrete particle of interest "Pi" 620 via respective bonds 621. There can be more or less than three other discrete particles "Pj" 628 within the domain of influence of the discrete particle of interest "Pi" 620. The location of the discrete particle of interest "Pi" 620 is indicated with a vector "$r_i$" 622, while the location of each of the other discrete particles is indicated with a vector "$r_j$" 624. The first configuration can be a snapshot at a particular time in time-marching simulation of the physical domain.

Figure 6B:
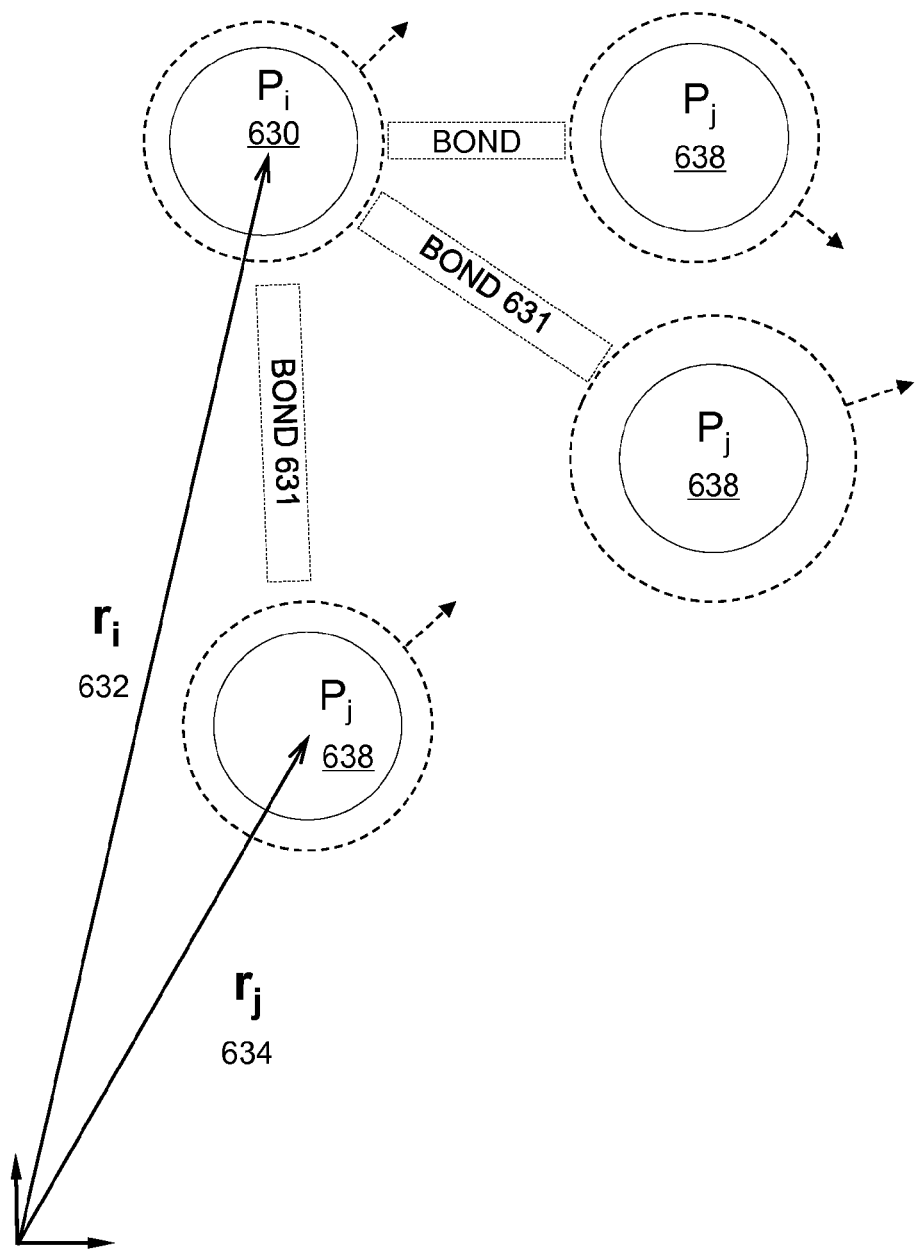
FIG. 6B is a two-dimensional diagram showing a second exemplary configuration of the discrete particle of interest in FIG. 6A.

A second exemplary configuration is shown in FIG. 6B. The second exemplary configuration is at a later time of the first exemplary configuration. The corresponding discrete particle of interest "Pi" 630 and other discrete particles "Pj" 638 connected with respective bonds 631. Two location vectors "$r_i$" 632 and "$r_j$" 634 are for the new locations. It is noted that orientation and size of each discrete particle (indicated with dotted line in FIG. 6B) are different between the first and second configurations. Bonds 621, 631 are adjusted accordingly and subject to the rule of breakage, which is defined in a set of mathematical formula set forth in the following paragraphs.

Each discrete particle has its own initial location, orientation, and size (e.g., volume in three-dimension (3-D) or area in two-dimension (2-D)) as the initial state. A bond is created for each pair of the particles within the domain of influence 404. Using a circle as an example, the domain of influence's radius R 414 is the characteristic dimension or influence distance.

After deformation in a time-marching simulation, each discrete particle may have moved to a second location (as movement u 311), a second orientation (as rotation ω 222), and/or a second size (as expansion/shrinkage θ 220).

The bonded-particle model for a physical domain (i.e., specific material) is defined as follows:

1. Material Properties

| | |
|---|---|
| Bulk Modulus | K |
| Shear Modulus | G |
| Young's Modulus | E = 9KG/(3K + G) |
| Poisson's Ratio | v = (3K − 2G)/2(3K + G) |
| Fracture Energy Release Rate | $G_c$ |

2. Each discrete particle "i" ("Pi" 620) with its neighboring discrete particles "j" ("Pj" 628) within the domain of influence

| | |
|---|---|
| Influence Distance (Characteristic dimension 414) | R |
| Initial Influence Volume | $V_i^0 = \sum_{j \in \Omega_i^0} V_j$ for $\forall j : \|r_j - r_i\| \leq R$ |
| Current Influence Volume | $V_i^t = \sum_{j \in \Omega_i^t} V_j$ for $\forall j : \|r_j - r_i\| \leq R$ |
| Particle Constants (3-D) | $c^k = 8(3K - 2G)/R$ |
| | $c^s = 8G/R$ |
| Particle Constants (2-D) | $c^k = 6E/(1 - v)/R$ |
| | $c^s = 12G/R$ |
| Critical Energy Density (3-D) | $w^{cs} = 5G_c/R$ |
| | $w^{ck} = w^{cs}/4$ |
| Critical Energy Density (2-D) | $w^{cs} = 3/2\pi G_c/R$ |
| | $w^{ck} = w^{cs}/5$ | where $\Omega_i^0$ is the domain of influence of discrete particle "i" initially while $\Omega_i^t$ is the domain of influence at a later time. $V_j$ is the volume of respective discrete particles located within the domain of influence.

3. Interactions between neighboring discrete particles include

1) Expansion $$\theta_i = \frac{1}{V_i^t} \sum_{j \in \Omega_i^t} V_j \frac{(r_j - r_i) \cdot (u_j - u_i)}{(r_j - r_i) \cdot (r_j - r_i)}$$

2) Rotation $$\omega_i = \frac{1}{V_i^t} \sum_{j \in \Omega_i^t} V_j \frac{(r_j - r_i) \times (u_j - u_i)}{(r_j - r_i) \cdot (r_j - r_i)}$$

3) Deformation Decomposition $$u_{ij}^k = (\theta_j + \theta_i)(r_j - r_i)/2$$

$$u_{ij}^r = (\omega_j + \omega_i) \times (r_j - r_i)/2$$

$$u_{ij}^p = u_j - u_i - u_{ij}^r$$

$$u_{ij}^n = \frac{u_{ij}^p \cdot (r_j - r_i)}{(r_j - r_i) \cdot (r_j - r_i)} (r_j - r_i)$$

$$u_{ij}^s = u_{ij}^p - u_{ij}^n$$

4) Force on each discrete particle $$f_i = \sum_{j \in \Omega_i} f_{ij}^k + f_{ij}^n + f_{ij}^s$$

$$f_{ij}^k = \frac{\sqrt{c_i^k c_j^k}}{\sqrt{V_i^0 V_j^0}} \frac{V_i V_j u_{ij}^k}{\|(r_j - r_i)\|}$$

$$f_{ij}^n = \frac{\sqrt{c_i^s c_j^s}}{\sqrt{V_i^0 V_j^0}} \frac{V_i V_j u_{ij}^n}{\|(r_j - r_i)\|}$$

-continued $$f_{ij}^s = \frac{\sqrt{c_i^s c_j^s}}{\sqrt{V_i^0 V_j^0}} \frac{V_i V_j u_{ij}^s}{\|(r_j - r_i)\|}$$

5) Deformation Energy Density $$w_{ij}^k = \frac{1}{2}\left(\sqrt{c_i^k c_j^k}\, u_{ij}^k \cdot u_{ij}^k\right) / [(r_j - r_i)\cdot(r_j - r_i)]$$

$$w_{ij}^n = \frac{1}{2}\left(\sqrt{c_i^n c_j^n}\, u_{ij}^n \cdot u_{ij}^n\right) / [(r_j - r_i)\cdot(r_j - r_i)]$$

$$w_{ij}^s = \frac{1}{2}\left(\sqrt{c_i^s c_j^s}\, u_{ij}^s \cdot u_{ij}^s\right) / [(r_j - r_i)\cdot(r_j - r_i)]$$

6) Rule for breakage of a bond—A bond breaks if the following critical value is reached:

$$w_{ij}^k/\sqrt{w_i^{ck} w_j^{ck}} + w_{ij}^n/\sqrt{w_i^{cs} w_j^{cs}} + w_{ij}^s/\sqrt{w_i^{cs} w_j^{cs}} \geq 1$$

if the bond is in compression $(u_{ij}^k + u_{ij}^n)\cdot(r_j - r_i) \geq 0$ $$w_{ij}^s/\sqrt{w_i^{cs} w_j^{cs}} \geq 1$$

if the bond is in compression $(u_{ij}^k + u_{ij}^n)\cdot(r_j - r_i) \geq 0$

Fracture energy release rate $G_c$ is the energy dissipated during fracture per unit of newly created fracture surface area and can be obtained via well known techniques, for example, a material property test.

Referring back to FIG. 1, at step 108, process 100 obtains numerically simulated continuum physical phenomena (e.g., cracking of a brittle material) of the physical domain under a loading condition by conducting a time-marching simulation using the plurality of discrete particles and associated bonded-particle model. The time-marching simulation starts at time zero (i.e., initial condition) and marching forward with a time increment in each of a number of solution cycles until a predetermined condition has been met. Each solution cycle corresponds to a specific time. Behaviors of the discrete particles are governed by the bonded-particle model.

Figure 9:
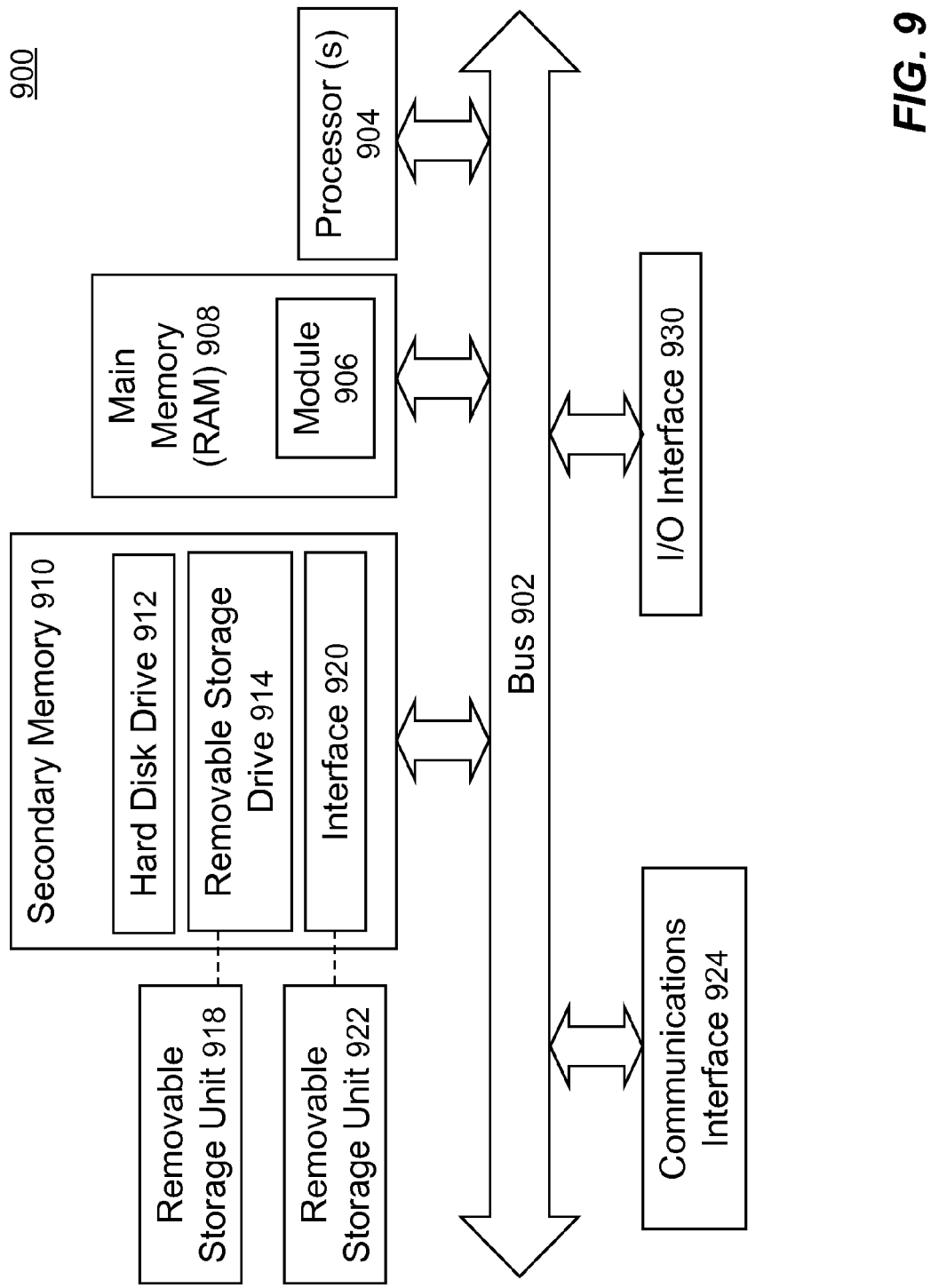
FIG. 9 is a function diagram showing salient components of a computing device, in which an embodiment of the present invention may be implemented.

According to one aspect, the present invention is directed towards one or more computer systems capable of carrying out the functionality described herein. An example of a computer system 900 is shown in FIG. 9. The computer system 900 includes one or more processors, such as processor 904. The processor 904 is connected to a computer system internal communication bus 902. Various software embodiments are described in terms of this exemplary computer system. After reading this description, it will become apparent to a person skilled in the relevant art(s) how to implement the invention using other computer systems and/or computer architectures.

Computer system 900 also includes a main memory 908, preferably random access memory (RAM), and may also include a secondary memory 910. The secondary memory 910 may include, for example, one or more hard disk drives 912 and/or one or more removable storage drives 914, representing a floppy disk drive, a magnetic tape drive, an optical disk drive, etc. The removable storage drive 914 reads from and/or writes to a removable storage unit 918 in a well-known manner. Removable storage unit 918, represents a floppy disk, magnetic tape, optical disk, etc. which is read by and written to by removable storage drive 914. As will be appreciated, the removable storage unit 918 includes a computer usable storage medium having stored therein computer software and/or data.

In alternative embodiments, secondary memory 1110 may include other similar means for allowing computer programs or other instructions to be loaded into computer system 900. Such means may include, for example, a removable storage unit 922 and an interface 920. Examples of such may include a program cartridge and cartridge interface (such as that found in video game devices), a removable memory chip (such as an Erasable Programmable Read-Only Memory (EPROM), Universal Serial Bus (USB) flash memory, or PROM) and associated socket, and other removable storage units 922 and interfaces 920 which allow software and data to be transferred from the removable storage unit 922 to computer system 900. In general, Computer system 900 is controlled and coordinated by operating system (OS) software, which performs tasks such as process scheduling, memory management, networking and I/O services.

There may also be a communications interface 924 connecting to the bus 902. Communications interface 924 allows software and data to be transferred between computer system 900 and external devices. Examples of communications interface 924 may include a modem, a network interface (such as an Ethernet card), a communications port, a Personal Computer Memory Card International Association (PCMCIA) slot and card, etc. Software and data transferred via communications interface 924 are in the form of signals 928 which may be electronic, electromagnetic, optical, or other signals capable of being received by communications interface 924. The computer 900 communicates with other computing devices over a data network based on a special set of rules (i.e., a protocol). One of the common protocols is TCP/IP (Transmission Control Protocol/Internet Protocol) commonly used in the Internet. In general, the communication interface 924 manages the assembling of a data file into smaller packets that are transmitted over the data network or reassembles received packets into the original data file. In addition, the communication interface 924 handles the address part of each packet so that it gets to the right destination or intercepts packets destined for the computer 900. In this document, the terms "computer program medium" and "computer usable medium" are used to generally refer to media such as removable storage drive 914, and/or a hard disk installed in hard disk drive 912. These computer program products are means for providing software to computer system 900. The invention is directed to such computer program products.

The computer system 900 may also include an input/output (I/O) interface 930, which provides the computer system 900 to access monitor, keyboard, mouse, printer, scanner, plotter, and alike.

Computer programs (also called computer control logic) are stored as application modules 906 in main memory 908 and/or secondary memory 910. Computer programs may also be received via communications interface 924. Such computer programs, when executed, enable the computer system 900 to perform the features of the present invention as discussed herein. In particular, the computer programs, when executed, enable the processor 904 to perform features of the present invention. Accordingly, such computer programs represent controllers of the computer system 900.

In an embodiment where the invention is implemented using software, the software may be stored in a computer program product and loaded into computer system 900 using removable storage drive 914, hard drive 912, or communications interface 924. The application module 906, when executed by the processor 904, causes the processor 904 to perform the functions of the invention as described herein.

The main memory 908 may be loaded with one or more application modules 906 (e.g., discrete element method) that can be executed by one or more processors 904 with or without a user input through the I/O interface 930 to achieve desired tasks. In operation, when at least one processor 904 executes one of the application modules 906, the results are computed and stored in the secondary memory 910 (i.e., hard disk drive 912). The result and/or status of the finite element analysis (e.g., crack propagation) is reported to the user via the I/O interface 930 either in a text or in a graphical representation to a monitor coupled to the computer.

Although the present invention has been described with reference to specific embodiments thereof, these embodiments are merely illustrative, and not restrictive of, the present invention. Various modifications or changes to the specifically disclosed exemplary embodiments will be suggested to persons skilled in the art. Whereas the discrete particles have been generally shown in two-dimension for illustration simplicity, the present invention can be applied to a three-dimensional particle, for example, a sphere. In summary, the scope of the invention should not be restricted to the specific exemplary embodiments disclosed herein, and all modifications that are readily suggested to those of ordinary skill in the art should be included within the spirit and purview of this application and scope of the appended claims.

What is claimed is:

1. A method of providing a bonded-particle model amongst a plurality of discrete particles representing a physical domain in a time-marching simulation to obtain numerically simulated continuum physical phenomena, the method comprising:
    receiving a definition of a plurality of discrete particles representing a physical domain made of brittle material in a computer system having an application module installed thereon;
    assigning a domain of influence to each discrete particle;
    associating a bonded-particle model for the plurality of discrete particles with physical properties of the physical domain, said bonded-particle model defining respective bonds to connect said each discrete particle and another one or more of the discrete particles within the domain of influence of said each discrete particle and defining a rule for determining bond breakage, wherein the physical properties include deformations and fracture energy release rate; and
    obtaining numerically simulated continuum physical phenomena by conducting a time-marching simulation of the physical domain subject to a loading condition using the discrete particles whose behaviors are governed by the bonded-particle model.

2. The method of claim 1, wherein said definition of the plurality of discrete particles comprises an initial location, orientation and size of said each discrete particle.

3. The method of claim 1, wherein said bonded-particle model further comprises moving said each discrete particle from a first location to a second location; expanding or shrinking of said each particle from a first size to a second size; and self-rotating about said each particle's center from a first orientation to a second orientation during the time-marching simulation.

4. The method of claim 1, wherein the said fracture energy release rate is obtained from a material property test of a specimen of said brittle material.

5. The method of claim 1, wherein said loading condition comprising a tensile force to tear a crack of the physical domain.

6. The method of claim 5, wherein said continuum physical phenomena comprise crack propagations in the physical domain.

7. The method of claim 1, wherein the rule is based on a set of critical deformation energy densities derived from relative deformations between each pair of the discrete particles.

8. The method of claim 7, wherein the set of critical deformation energy densities further depends upon a characteristic dimension of said each discrete particle and the fracture energy release rate, wherein the characteristic dimension is used for define the domain of influence.

9. A system for providing a bonded-particle model amongst a plurality of discrete particles representing a physical domain in a time-marching simulation to obtain numerically simulated continuum physical phenomena, the system comprising:
    a main memory for storing computer readable code for an application module;
    at least one processor coupled to the main memory, said at least one processor executing the computer readable code in the main memory to cause the application module to perform operations by a method of:
    receiving a definition of a plurality of discrete particles representing a physical domain made of brittle material;
    assigning a domain of influence to each discrete particle;
    associating a bonded-particle model for the plurality of discrete particles with physical properties of the physical domain, said bonded-particle model defining respective bonds to connect said each discrete particle and another one or more of the discrete particles within the domain of influence of said each discrete particle and defining a rule for determining bond breakage, wherein the physical properties include deformations and fracture energy release rate; and
    obtaining numerically simulated continuum physical phenomena by conducting a time-marching simulation of the physical domain subject to a loading condition using the discrete particles whose behaviors are governed by the bonded-particle model.

10. The system of claim 9, wherein said definition of the plurality of discrete particles comprises an initial location, orientation and size of said each discrete particle.

11. The system of claim 9, wherein said bonded-particle model further comprises moving said each discrete particle from a first location to a second location; expanding or shrinking of said each particle from a first size to a second size; and self-rotating about said each particle's center from a first orientation to a second orientation during the time-marching simulation.

12. The system of claim 9, wherein the said fracture energy release rate is obtained from a material property test of a specimen of said brittle material.

13. The system of claim 9, wherein the rule is based on a set of critical deformation energy densities derived from relative deformations between each pair of the discrete particles.

14. The system of claim 13, wherein the set of critical deformation energy densities further depends upon a characteristic dimension of said each discrete particle and the fracture energy release rate, wherein the characteristic dimension is used for define the domain of influence.

15. A non-transitory computer recordable storage medium containing computer instructions for providing a bonded-particle model amongst a plurality of discrete particles representing a physical domain in a time-marching simulation to obtain numerically simulated continuum physical phenomena, said computer instructions when executed on a computer system cause the computer system to perform the steps of:

receiving a definition of a plurality of discrete particles representing a physical domain made of brittle material in a computer system having an application module installed thereon;

assigning a domain of influence to each discrete particle;

associating a bonded-particle model for the plurality of discrete particles with physical properties of the physical domain, said bonded-particle model defining respective bonds to connect said each discrete particle and another one or more of the discrete particles within the domain of influence of said each discrete particle and defining a rule for determining bond breakage, wherein the physical properties include deformations and fracture energy release rate; and obtaining numerically simulated continuum physical phenomena by conducting a time-marching simulation of the physical domain subject to a loading condition using the discrete particles whose behaviors are governed by the bonded-particle model.

16. The non-transitory computer recordable storage medium of claim 15, wherein said definition of the plurality of discrete particles comprises an initial location, orientation and size of said each discrete particle.

17. The non-transitory computer recordable storage medium of claim 15, wherein said bonded-particle model further comprises moving said each discrete particle from a first location to a second location; expanding or shrinking of said each particle from a first size to a second size; and self-rotating about said each particle's center from a first orientation to a second orientation during the time-marching simulation.

18. The non-transitory computer recordable storage medium of claim 15, wherein the said fracture energy release rate is obtained from a material property test of a specimen of said brittle material.

19. The non-transitory computer recordable storage medium of claim 15, wherein the rule is based on a set of critical deformation energy densities derived from relative deformations between each pair of the discrete particles.

20. The non-transitory computer recordable storage medium of claim 19, wherein the set of critical deformation energy densities further depends upon a characteristic dimension of said each discrete particle and the fracture energy release rate, wherein the characteristic dimension is used for define the domain of influence.

* * * * *